United States Patent [19]
Colvin

[11] Patent Number: 5,456,124
[45] Date of Patent: Oct. 10, 1995

[54] PROBE FOR EXHAUST GAS SAMPLING

[75] Inventor: Alex D. Colvin, Oak Park, Mich.

[73] Assignee: Ford Motor Company, Dearborn, Mich.

[21] Appl. No.: 218,773

[22] Filed: Mar. 28, 1994

[51] Int. Cl.⁶ ........................................... G01L 3/26
[52] U.S. Cl. ........................... 73/863.110; 73/116
[58] Field of Search .................... 73/232, 31.05, 73/23.32, 863.11, 116, 117.3, 863.81, 863.86, 864.15

[56] References Cited

U.S. PATENT DOCUMENTS

| | | |
|---|---|---|
| 3,958,527 | 5/1976 | Iannacone . |
| 4,328,780 | 5/1982 | Andrew .................................. 73/23.32 |
| 4,379,402 | 4/1983 | Harman, III ................................. 73/23 |
| 4,381,666 | 5/1983 | Feiertag . |
| 4,555,942 | 12/1985 | Ludvigsson . |
| 5,138,163 | 9/1992 | Butler et al. ................................. 73/116 |

FOREIGN PATENT DOCUMENTS

| | | |
|---|---|---|
| 0407283 | 1/1991 | European Pat. Off. . |
| 2004530 | 8/1971 | Germany . |
| 2210827 | 4/1973 | Germany . |
| 2351433 | 7/1974 | Germany . |
| 2721236 | 11/1977 | Germany . |
| 3030374 | 2/1982 | Germany . |
| 8815690 U | 3/1990 | Germany . |
| 3939450 | 6/1991 | Germany . |
| 280910 | 9/1970 | U.S.S.R. . |

Primary Examiner—Richard E. Chilcot, Jr.
Assistant Examiner—Max H. Noori
Attorney, Agent, or Firm—Peter Abolins; Roger L. May

[57] ABSTRACT

Exhaust gas constituents of an exhaust gas stream are measured by drawing a proportional sample of exhaust gas through a capillary tube inserted into the exhaust gas stream. The capillary tube is controllably heated to avoid distortion of the reading due to condensation. The mass flowing in the capillary tube is determined by sensing the pressure drop across the length of the capillary tube.

1 Claim, 2 Drawing Sheets

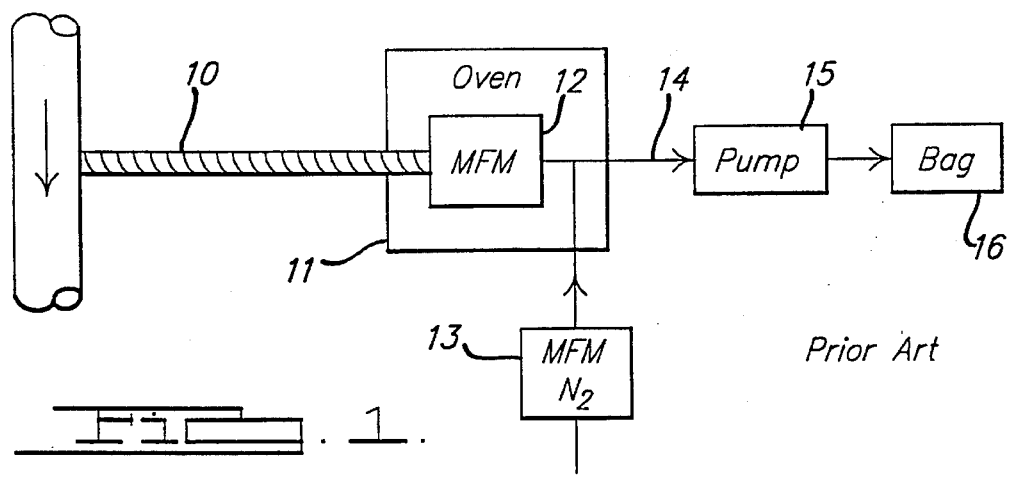
FIG. 1. *Prior Art*
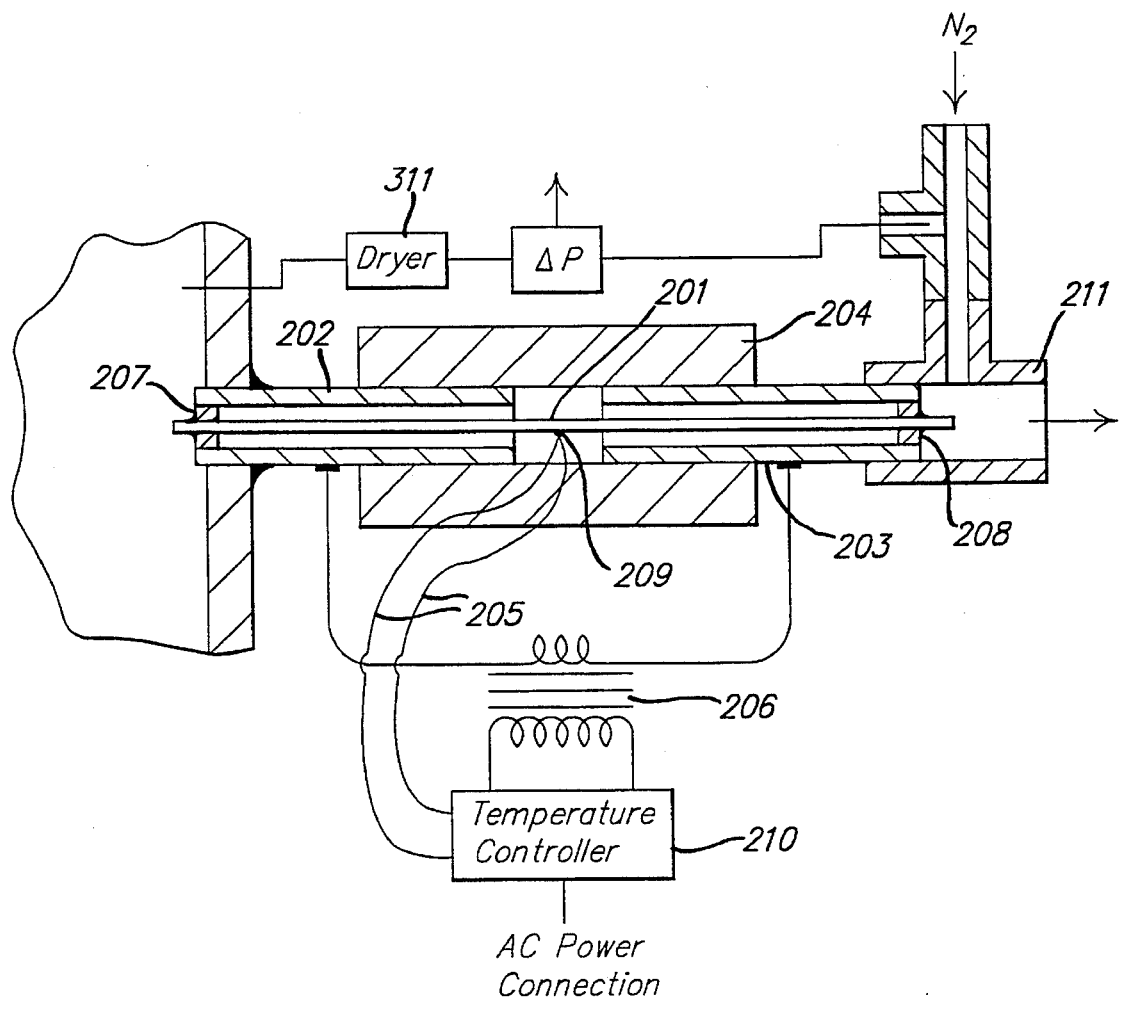
FIG. 2.

PROBE FOR EXHAUST GAS SAMPLING

BACKGROUND OF INVENTION

1. Field of the Invention

This invention relates to sampling the exhaust gas from the internal combustion engine.

2. Prior Art

As hydrocarbon exhaust gas levels are reduced to meet ever more stringent government regulations, the levels in vehicle exhaust gas actually approach those in ambient air. This makes accurate measurements of exhaust species at these lower concentration levels more difficult and requires the development of new measurement and sampling technologies. One solution to the sampling issue is use of what is referred to as a "mini-diluter." The analyses themselves are carried out on diluted exhaust gas (to prevent water condensation) at close to ambient temperature. To avoid condensation it is necessary to keep the exhaust gas temperature above its dew point until the dilution is made.

The current solution to this problem is to use heated sample lines. During "cold start," the connection between the cold exhaust pipe and the heated sample line is cold and may take a few minutes or more to heat up because of the low sample flow rate. Even if the connection between the heated sample line and the exhaust pipe is heated with a heating tape, it is hard to heat the very end of the connection. The probe described in this patent application avoids this problem.

Further, it is necessary to maintain the sampled exhaust gas in a heated state until both the mass of the sample is known and the sample has been diluted so that it does not have to be maintained in a heated state to be accurately analyzed. Further, it is known to measure the exhaust flow using two hot wire anemometers, one in the make up air, and the other in the diluted exhaust. This method of measuring the exhaust flow has the inherent error of subtracting two large values which are almost equal at idle and low flow conditions.

Referring to FIG. 1, in the prior art, a heated sample line 10 is about 7 to 10 feet long and is coupled to an oven 11 which contains a mass flow meter 12. After mass flow meter 12 measures the sample exhaust gas flow in the heated sample line 10, a diluting gas from a nitrogen mass flow meter 13 is added and flow proceeds down a tube 14 to a pump 15 and into a sample bag 16. It would be desirable to be able to substantially eliminate heated sample line 10, oven 11, and mass flow meter 12. These are some of the advantages the invention provides.

In summary, a mini-diluter is used to obtain a representative sample of engine exhaust gas for the purpose of calculating the mass of various emissions during an engine or vehicle test. This is achieved by taking an exhaust gas sample whose flow rate is proportional to the exhaust flow rate of the engine.

To avoid condensation of the water vapor in the exhaust the exhaust gas has to be diluted with dry gas such as nitrogen or zero air so that the dew point of the diluted mixture is lower than room temperature. To keep the concentration of the components to be measured high the dilution should not be greater than necessary. This means the dilution gas flow should also be proportional to the exhaust flow.

The advantages of a mini-diluter over other prior art systems include:

1. The dilution is made with pure gases rather than room air so background corrections are not needed.
2. The sample can be drawn anywhere in the exhaust system (such as feedgas or midbed) not just at the tailpipe.
3. A smaller amount of exhaust sample has to be handled (e.g. 0.1% versus 100%); no cooling or water trap are needed.
4. The concentration of exhaust gas in the mini-diluter bag can be 3 or 4 times that in other prior art system bags since the dilution is constant during the test. This makes the job of analysis easier.

SUMMARY OF INVENTION

This invention includes an improved mini-diluter with an improved exhaust gas sampling probe for use in analyzing exhaust gas in internal combustion engines. A mini-diluter draws a proportional sample of exhaust gas. That is, an amount is withdrawn which is proportional to the exhaust gas volume flow. To generate a proportional exhaust flow sample, the sample flow must be known before it is mixed or diluted with another gas. What is desired is to know the amount of any particular element or constituent of the exhaust gas (e.g. in grams). Using a proportional sample is easier than determining the concentration of any particular constituent and then multiplying it by the flow. Such multiplication is difficult because of the timing involved in determining both the concentration and the flow parameters. Multiplying the concentration by the flow can be avoided by using a mini-diluter and generating a diluted sample.

In accordance with an embodiment of this invention, a relatively short capillary tube is heated and has a measured pressure drop across its length, which provides an indication of flow. By measuring the pressure drop across the capillary tube for various flows a simple look-up table can be made for the sampling capillary. Further, not only is the capillary tube heated but it is kept at a known constant temperature so that there can even be a better indication of mass flow through the capillary. Such heating can control the amount of water by avoiding condensation, and to quantify how much flow there is through the capillary tube. This eliminates the need for the long heated sample line and the oven to keep the sample mass flow meter warm. Controlling the actual temperature is important so that the flow can be more accurately measured and determined.

Having a capillary sample tube is advantageous because there can be a pressure drop along the length of the capillary tube which can be measured. Further, it is easy to heat. That is, it is small, uniform, and can be configured to have an air insulating coat around it. Still further, the heat is applied exactly where it is needed, the mass flow through the capillary tube can be determined, and it is possible to eliminate the use of the oven and the sample mass flow meter. Thus the process is simplified, and accuracy is improved.

An advantage of this invention is that the exhaust gas sample is easily taken as a fixed known fraction of the total exhaust flow and then it gets diluted quickly which makes it easier to handle. That is, until the sample is diluted it has to be heated so that water in the sample does not condense. In accordance with an embodiment of this invention, the distance of travel which has to be heated is minimized to the length of the capillary tube. Further, this heating is done very accurately and efficiently without much heat loss.

In summary, comparing capillary sampling to prior art mass flow sampling, capillary sampling has the following advantages:

1. Heated capillary can be inserted into the exhaust pipe leaving no cool connection for exhaust gas sample condensation.
2. The heated capillary does not need an oven like the sample mass flow meter does.
3. The diluting gas can be added at a "T" at the end of the heated capillary. The heated sample line between the sample point and mini-diluter is not necessary.
4. The capillary pressure drop signal used for measuring the sample flow is about 20 times faster than prior art mass flowmeter signals. This allows for fast control of the sample and diluent flows in the mini-diluter system.
5. The sampling capillary can easily be kept at 200° or 300° C. Also the temperature can be raised to burn off any deposits.
6. The power requirements are about 10 times less than the oven and heated line.
7. The capillary is at operating temperature in a few seconds.
8. The inner diameter of the capillary is about 1 mm compared to about 0.2 mm for the mass flowmeter sensor tube. Therefore a filter will not be needed to protect the heated capillary.
9. Since the heated capillary is right at the sampling point there is no need to delay the start and stop of sampling to assure that the proper sample gets into the sampling bags. This is because the diluted sample travels much faster and its delay can be neglected.

DESCRIPTION OF DRAWINGS

FIG. 1 is a block diagram of a mini-diluter with a heated sample line in accordance with the prior art;

FIG. 2 is a simplified cross sectional diagram of an exhaust gas sample probe in accordance with an embodiment of this invention.

DETAILED DESCRIPTION OF THE INVENTION

Figure 3:
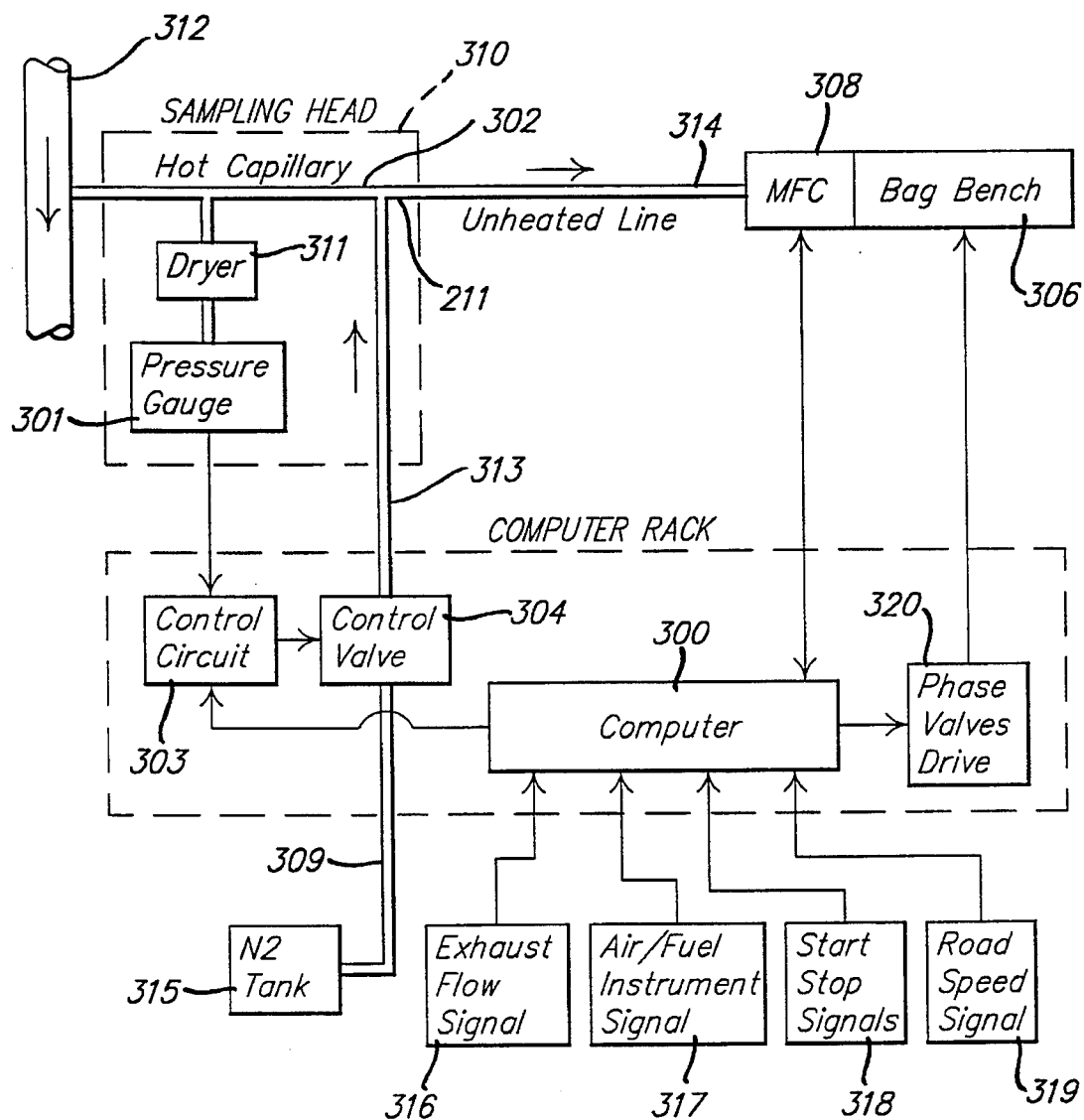
FIG. 3 is a block diagram of a mini-diluter using a sample probe in accordance with an embodiment of this invention.

Referring to FIG. 2, a stainless steel capillary tube 201 with an outer diameter of 0.0625 inches (in.) is placed inside and brazed, using brazes 207, 208, to the outside ends of two 0.25 in. outer diameter stainless steel outer tubes 202, 203 which are separated about 0.25 in. apart from each other. Outer tubes 202, 203 are supported by a 0.25 in. inner diameter teflon tube 204 for rigidity. Teflon tube 204 is slit to pass a thermocouple wire 205. A filament transformer 206, with a secondary capable of 10 amps and 1 volt provides power for heating capillary tube 201. The secondary leads are electrically connected to each of outer tubes 202, 203. The secondary current passes through brazes 207, 208 on each end and through capillary tube 201. A thermocouple 209 is spot welded to capillary tube 201 between the outer tubes 202, 203 to monitor the temperature of capillary tube 201. Thermocouple 209 provides the control signal to a temperature controller 210 which powers transformer 206 primary power to keep capillary tube 201 at the desired temperature.

A feature of this arrangement is that the exhaust gas sample passes through the center of capillary tube 201 which is heated by current passing through the capillary's wall and is thus heated along its entire length. No additional heating tapes or other heaters are needed. Outer tube 202 is inserted through a boss which is ordinarily welded on to the tailpipe or engine pipe for purposes of sampling. The sample probe can be made longer so as to protrude into the sample stream. After the exhaust gas sample passes through capillary tube 201, it is mixed with the dilutant gas in a "T" 211. The resulting diluted mixture can be transported without heated lines.

Referring to FIG. 3, a sampling head 310 includes a hot capillary tube 302 which is coupled to a dryer 311 and a pressure gauge 301 for determining a pressure drop across capillary tube 302. One end of capillary tube 302 is coupled to exhaust pipe 312 which carries the exhaust gas flow to be sampled. The other end of capillary tube 302 is coupled to a nitrogen supply line 313 and to an unheated line 314 which carries the mixed exhaust gas and nitrogen to a storage and analyzing system, including bench bag 306. A nitrogen tank 315 supplies nitrogen through a tube 309 to control valve 304. A computer 300 receives inputs from an exhaust flow signal block 316, an air/fuel instrument signal block 317, a start stop signal block 318, a road speed signal block 319. Computer 300 provides an output to a control circuit 303 for activating control valve 304 and a phase valves drive 320 for activating bag bench 306. Computer 300 is coupled by inputs and outputs to a mass flow control (M.F.C.) portion 308 for controlling flow into bag bench 306.

In operation, computer 300 receives an exhaust flow signal 316 characterizing exhaust gas flow and generates a desired delta pressure signal for control circuit 303. Control circuit 303 compares the desired delta signal pressure to the measured delta pressure signal measured by pressure transducer 301, and operates control valve 304 to control the flow of nitrogen from nitrogen tank 315 to the achieve the desired delta pressure.

Computer 300 also sends a signal to mass flow controller 308. The signal to mass flow controller 308 can be either a constant value (to mimic CVS sampling) or proportional to the exhaust flow (to achieve higher bag concentrations of the species being measured).

Various other modifications and variations will no doubt occur to those skilled in the art to which this invention pertains. Such modifications and variations which generally rely on the teachings through which this disclosure has advanced the art are properly considered within the scope of this invention.

I claim:

1. A mini-diluter system for sampling exhaust gases from an exhaust gas stream including:

a heated capillary tube having at least one end extending into an exhaust gas stream and having a generally cylindrical heated surface;

an insulating means surrounding the heated surface;

a temperature sensing means coupled to the heated surface of the capillary tube for providing a signal indicating the temperature of the capillary tube;

a temperature controller coupled to receive the signal from the temperature sensing means no control a current applied to the wall of the capillary tube so as to maintain the substantially constant temperature along the capillary tube;

a pressure differential sensor sensing a pressure drop across the length of the capillary tube so that the mass flowing the capillary tube can be determined;

flow sensing means for determining the flow of the exhaust gas stream and generating an output signal indicating the exhaust gas flow;

a computer means for receiving the exhaust gas flow signal and controlling the application of heating current to the capillary tube and for controlling the mixing of exhaust gas flow through the capillary tube with a known gas;

wherein said capillary tube is made of stainless steel material;

wherein said temperature controller includes a first and a second conductive tube, one being electrically coupled to each end of said capillary tube for applying a heating current to said capillary tube;

a nitrogen tank for supplying a source of nitrogen to mix with the exhaust gas;

a fluid flow path means coupled between said nitrogen tank and the fluid flow from said capillary tube;

a control valve coupled to said fluid flow path means for controlling nitrogen flow; and a control circuit coupled to said computer means and said control valve for actuating said control valve in response to signals from said computer means; further comprising a bag means for storing fluid flow downstream of the mixing of the exhaust gas flow with the nitrogen, said bag means being coupled to said computer means for facilitating analysis the stored gas.

* * * * *